(12) United States Patent
Lampert et al.

(10) Patent No.: US 7,074,375 B2
(45) Date of Patent: Jul. 11, 2006

(54) METHOD OF DESULFURIZING A HYDROCARBON GAS BY SELECTIVE PARTIAL OXIDATION AND ADSORPTION

(75) Inventors: Jordan K. Lampert, Metuchen, NJ (US); Lawrence Shore, Edison, NJ (US); Robert J. Farrauto, Princeton, NJ (US); Shinn Hwang, Livingston, NJ (US)

(73) Assignee: Engelhard Corporation, Iselin, NJ (US)

( * ) Notice: Subject to any disclaimer, the term of this patent is extended or adjusted under 35 U.S.C. 154(b) by 477 days.

(21) Appl. No.: 10/308,356

(22) Filed: Dec. 3, 2002

(65) Prior Publication Data

US 2004/0106837 A1 Jun. 3, 2004

(51) Int. Cl.
*B01D 53/86* (2006.01)
*C01B 3/38* (2006.01)
*C01B 31/18* (2006.01)

(52) U.S. Cl. ............ 423/244.09; 252/373; 423/244.02; 423/244.1; 423/418.2; 423/651; 423/652

(58) Field of Classification Search ........... 423/244.01, 423/244.04, 244.09–244.1, 418.2, 651, 652; 48/197 R, 198.1, 198.7, 212, 215, 213; 252/373
See application file for complete search history.

(56) References Cited

U.S. PATENT DOCUMENTS

| | | | |
|---|---|---|---|
| 1,900,751 A | 3/1933 | Baehr | |
| 4,117,100 A | 9/1978 | Hellmer et al. | 423/569 |
| 4,123,507 A | 10/1978 | Hass | 423/573 G |
| 4,243,647 A | 1/1981 | Hass et al. | 423/573 G |
| 4,699,631 A | 10/1987 | Marion | 48/197 R |
| 4,776,860 A * | 10/1988 | Najjar et al. | 48/197 R |
| 4,801,438 A * | 1/1989 | Najjar et al. | 423/230 |
| 4,801,440 A * | 1/1989 | Najjar et al. | 423/418.2 |
| 4,808,386 A | 2/1989 | Najjar et al. | 423/226 |
| 4,851,152 A * | 7/1989 | Najjar | 252/373 |
| 4,925,644 A | 5/1990 | Najjar et al. | 423/415 |
| 4,957,544 A * | 9/1990 | Najjar | 75/500 |
| 5,250,083 A | 10/1993 | Wolfenbarger et al. | |
| 5,292,428 A * | 3/1994 | Harrison et al. | 208/208 R |
| 5,514,351 A | 5/1996 | Buchanan et al. | 423/220 |
| 5,516,344 A * | 5/1996 | Corrigan | 48/127.9 |
| 5,720,901 A | 2/1998 | De Jong et al. | 252/373 |
| 6,171,478 B1 | 1/2001 | Cabrera et al. | |
| 6,221,280 B1 * | 4/2001 | Anumakonda et al. | 252/372 |
| 6,277,271 B1 | 8/2001 | Kocal | 208/212 |
| 6,299,994 B1 | 10/2001 | Towler et al. | 429/17 |
| 6,340,437 B1 * | 1/2002 | Yagi et al. | 252/373 |
| 6,403,051 B1 | 6/2002 | Keller | 423/573.1 |
| 6,521,204 B1 * | 2/2003 | Borup et al. | 423/652 |
| 6,726,850 B1 * | 4/2004 | Reyes et al. | 252/373 |

FOREIGN PATENT DOCUMENTS

| | | |
|---|---|---|
| DE | 34 43 686 A1 | 5/1986 |
| EP | 0 842 894 * | 5/1998 |
| GB | 2 274 284 * | 7/1994 |

OTHER PUBLICATIONS

DERWENT abstract accession No. 1987-151171, for DE 3443686, published Jun. 1986.*
EP abstract publication No. DE003443686A1, for DE 3443686, published Jun. 1986.*
EP Examination Report for EP Appln. No. 03 787 216.5, dated Oct. 7, 2005, with copy of examined claims attached, 6 pp. total.*

* cited by examiner

*Primary Examiner*—Stanley S. Silverman
*Assistant Examiner*—Ardith E. Hertzog
(74) *Attorney, Agent, or Firm*—Raymond F. Keller

(57) ABSTRACT

A hydrocarbon gas such as methane and LPG is desulfurized in the presence of oxygen and an oxidation catalyst to convert sulfur compounds in the gas to sulfur oxides. The sulfur oxides are then trapped downstream of the oxidation by an adsorbent. The amount of oxygen added to the hydrocarbon gas to promote oxidation is such that the sulfur compounds are selectively oxidized and the oxidation of the hydrocarbon gas is minimized to reduce hydrogen formation.

29 Claims, 1 Drawing Sheet

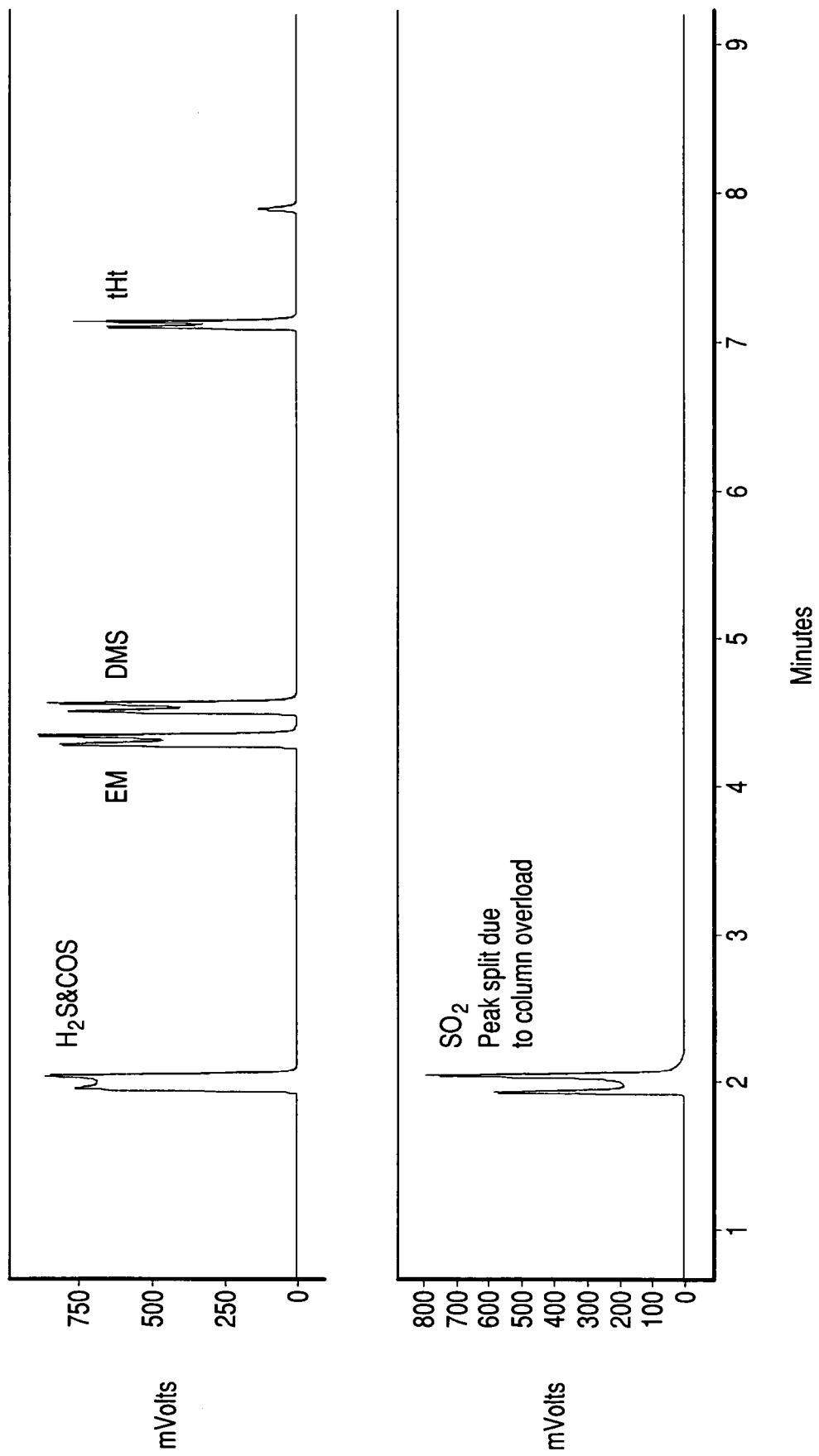

METHOD OF DESULFURIZING A HYDROCARBON GAS BY SELECTIVE PARTIAL OXIDATION AND ADSORPTION

BACKGROUND OF THE INVENTION

1. Field of the Invention

The present invention relates to an improved system for reducing sulfur compound content in a hydrocarbon gas stream. More particularly, the desulfurizing system described herein may be used to reduce the presence of inorganic and organic sulfur compounds in the gas stream to levels acceptable for, e.g., subsequent reforming of the hydrocarbon.

2. Discussion of the Prior Art

The partial oxidation of hydrocarbons, for example, methane, in the presence of a catalyst is an attractive route for the preparation of mixtures of carbon monoxide and hydrogen, known in the art as synthesis gas. The partial oxidation of a hydrocarbon is an exothermic reaction and, in the case in which methane is the hydrocarbon, proceeds by the following reaction (1):

$$2CH_4 + O_2 \rightarrow 2CO + 4H_2 \quad (1)$$

Another important source of hydrogen and synthesis gas is derived from steam reforming a hydrocarbon such as methane. Catalyzed steam reforming is endothermic and in the case in which methane is the hydrocarbon, proceeds by the following reaction (2):

$$CH_4 + H_2O \rightarrow CO + 3H_2 \quad (2)$$

It is well known and desirable to reduce the level of gaseous sulfur compounds such as hydrogen sulfide ($H_2S$), carbonylsulfide (COS), mercaptans (R—SH), and sulfides ($R^1$—S—$R^2$) from hydrocarbon streams prior to reforming the hydrocarbon stream into useful gaseous components such as by either of reactions (1) and (2) above. Many applications, e.g., fuel cells, require that the gaseous sulfur compounds in a gas stream (e.g., naphtha, liquid petroleum gas (LPG), town gas, etc.) be reduced to as low a level as practicable in order to avoid polluting the environment or poisoning (i.e., deactivating) catalysts such as steam reforming catalysts, water-gas shift catalysts, etc. Fuels, such as natural gas, gasoline, diesel fuel, naphtha, fuel oil, LPG and like hydrocarbon fuels may not be useful as a process fuel source due to the existence of relatively high levels of naturally-occurring complex organic sulfur compounds, or sulfur compounds added as odorants, such as mercaptans and sulfides.

Desulfurization of hydrocarbon streams is particularly beneficial for hydrogen generation and use thereof in fuel cells. Conventional fuel processing systems used with stationary fuel cell power plants include a thermal steam reformer, such as that described in U.S. Pat. No. 5,516,344. In such a fuel processing system, sulfur is removed by conventional hydrodesulfurization techniques, which typically rely on a certain level of recycle as a source of hydrogen for the process. The recycle hydrogen combines with the organic sulfur compounds to form hydrogen sulfide within a catalytic bed. The hydrogen sulfide is then removed using a zinc oxide bed to form zinc sulfide. A general hydrodesulfurization process is disclosed in detail in U.S. Pat. No. 5,292,428. There are many such prior art processes involving hydrogenation desulfurization in which the sulfur compounds in the fuel stream are decomposed by hydrogenolysis at temperatures of, e.g., 350 to 400° C. in the presence of e.g., Ni—Mo or Co—Mo catalysts and thereafter the resultant $H_2S$ is then absorbed on a bed of ZnO at temperatures of, e.g., 300 to 400° C. However, in these processes, the level of the $H_2S$ remaining in the treated stream is often too high, e.g., 1 ppmV and higher. It is well known low levels of gaseous sulfur compounds will deactivate steam reforming nickel-based catalysts. Additionally, to remove the sulfur compounds from the gas being treated, hydrogen must be provided to the gas stream. In the case where the source of hydrogen is product gas in the form of recycle, this will reduce the overall efficiency of the power forming process.

Hydrogen sulfide has also been removed from gas streams by passing the gas stream through a liquid scrubber, such as sodium hydroxide, potassium hydroxide, or amines. Liquid scrubbers are large and heavy, and require large chemical inventories. Clean-up of the product gas is often needed to prevent carryover of the base scrubbing chemicals.

Still another process for removing sulfur compounds from hydrocarbon gas streams involves passing the gas stream directly through an adsorbent, which captures the sulfur species. Although the adsorption process operates at moderate temperatures and atmospheric pressure, a large inventory of adsorbent is needed. For natural gas, large volumes of one or more adsorbents are required for reasonable time on stream, e.g., one year, typically up to 20 liters total volume for a 2.5 kilowatt electric (kWe) average output fuel cell. Furthermore, natural gas composition variability makes choosing the appropriate adsorbents and bed sizes complicated and costly. For LPG, desulfurization by adsorption is particularly difficult due to the potentially high sulfur concentrations in LPG and adsorption interferences from LPG hydrocarbons.

SUMMARY OF THE INVENTION

The present invention provides a process for the removal of sulfur compounds from a hydrocarbon feedstock. The process generally involves passing a hydrocarbon feed with a sub-stoichiometric amount of an oxygen-containing gas over an oxidation catalyst such that at least a portion of the sulfur compounds in the hydrocarbon feed are converted to $SO_x$ without substantial oxidation of the hydrocarbons. An adsorbent placed downstream of the oxidation catalyst captures and removes the $SO_x$ compounds from the hydrocarbon feed. Once desulfurized, the hydrocarbon feed may be reformed to desired products such as hydrogen.

BRIEF DESCRIPTION OF THE DRAWiNG

The FIGURE is the output of a gas chromatography analysis of the inlet gas (top) and outlet gas (bottom) over a partial oxidation catalyst.

DETAILED DESCRIPTION OF THE INVENTION

The process detailed herein may be used to desulfurize any gaseous hydrocarbon containing gaseous sulfur compounds, including vaporized liquid hydrocarbons. The process is particularly suitable for the desulfurization of methane, natural gas, associated gas or other sources of light hydrocarbons, including LPG. In this respect, the term "light hydrocarbons" is a reference to hydrocarbons having from 1 to 5 carbon atoms. The process may be applied in the conversion of naturally occurring reserves of methane, which can contain sulfur concentrations on the order of 20 ppmV in the form of organic sulfur compounds, such as mercaptans and sulfides, and inorganic sulfur compounds, such as hydrogen sulfide, carbonyl sulfide, and carbon disulfide. An LPG feed can contain up to 200 ppmV of these sulfur compounds. The sulfur content of the hydrocarbon feed should be less than 100 ppbV, preferably less than 10 ppbV, to avoid poisoning of the reforming catalyst and adversely affecting end uses of the synthesis gas produced.

In accordance with one embodiment of the process, oxygen ($O_2$) is introduced into a hydrocarbon feedstock that is to be desulfurized, and the mixture is contacted with an oxidation catalyst. Air may be used as the oxygen source. An $O_2/C$ ratio is established so as to favor the oxidation of the sulfur compounds to $SO_x$ when the oxidation catalyst is contacted. For example, in the case of the hydrocarbon methane, as the $O_2/C$ ratio approaches stoichiometric levels with respect to methane partial oxidation reaction (1), $H_2S$ formation begins to supplant $SO_x$ formation due to reaction of the sulfur compounds with hydrogen. Therefore, the oxygen concentration relative to the hydrocarbon feed is controlled to limit reaction (1) and favor the selective oxidation of the sulfur compounds to $SO_x$.

The gaseous mixture contacted with the catalyst in the process of this invention typically comprises a plurality of different sulfur-containing compounds. Both organic and inorganic sulfur-containing compounds may be present. Examples of inorganic sulfur compounds that may be present include hydrogen sulfide, carbonyl sulfide, and carbon disulfide. Organic sulfur-containing compounds such as mercaptans and sulfides may also be contained in the hydrocarbon stream being treated.

The content of sulfur-containing compounds in the hydrocarbon feed can vary widely, and is typically in the range of from 0.05 to 170 ppmV in terms of sulfur (S) content. For natural gas, a sulfur content of 0.1 to 10 ppmV is more typical. For LPG, a sulfur compound content of from 10 to 170 ppmV is more typical. Hydrocarbon feed stocks obtained directly from naturally occurring reservoirs may have a sulfur compound content significantly above the aforementioned upper limits and will also benefit from the sulfur removal treatment described herein.

The hydrocarbon feedstock, oxygen and its associated gases and the sulfur-containing compounds are preferably well mixed prior to being contacted with the catalyst.

The oxygen-containing gas, preferably air, is added and mixed with the hydrocarbon feed in an amount sufficient to establish a suitable oxygen-to-carbon ratio to provide the selective oxidation of sulfur compounds and minimize the partial oxidation of hydrocarbons to hydrogen. In this process, the sulfur compounds are preferentially converted to $SO_x$, which can be readily captured downstream by an adsorbent. The addition of excess air leads to oxidation of the hydrocarbons and formation of hydrogen, which in turn leads to formation of hydrogen sulfide, which can be captured by zinc oxide or other suitable adsorbent. Thus, depending on the oxygen to carbon ratio, both $SO_x$ and $H_2S$ species may be present in the gas exiting the catalyst and then trapped downstream using a combination of $SO_x$ and $H_2S$ adsorbents.

The oxygen content of the hydrocarbon stream is characterized as sub-stoichiometric. What this means is that the ratio of the molecular oxygen ($O_2$) content relative to the carbon (C) atoms present in the hydrocarbon feedstock is less than that required for completion of reaction (1), i.e., less than 0.5. Preferably, the oxygen-to-carbon ratio is less than 0.3, more preferably from 0.01 to 0.08. There is a gradual increase in the formation of $H_2S$ at $O_2/C$ ratios above 0.04. Therefore, most preferably, the $O_2/C$ ratio should not exceed 0.04. If the $O_2/C$ ratio in the hydrocarbon feed is within the substoichiometric range contemplated herein without the addition of air or some other oxygen source, no additional oxygen need be introduced, though oxygen may still be added to establish a higher $O_2/C$ ratio within the contemplated range.

The process may be effectively operated at ambient pressure. However, since some hydrocarbon gases, in particular, vaporized liquid gases are supplied at elevated pressures, the process of the present invention may be operated at elevated pressures, that is pressures significantly above atmospheric pressure. Thus, the process may be operated at the vapor pressure of LPG.

The process may be operated at any suitable temperature. However, under the conditions of pressure prevailing in the process, it is necessary to allow the feed gases to contact the catalyst at elevated temperatures in order to achieve the level of conversion required for a commercial scale operation. Accordingly, the process is preferably operated at a temperature of at least 200° C. Preferably, the operating temperature is in the range of from 200° C. to 600° C., more preferably in the range of from 250° C. to 400° C. Temperatures in the range of from 275° C. to 375° C. are particularly suitable.

The feed mixture may be provided during the process at any suitable gas space velocity. It is an advantage of the process of the present invention that high gas space velocities may be applied. Thus, typical space velocities for the process are in the range of from 1,000 to 50,000/hr, more preferably in the range of from 5,000 to 20,000/hr.

Catalyst compositions suitable for use in the process are not particularly limited, so long as the composition can catalyze oxidation of sulfur compounds contained in the hydrocarbon feed to $SO_x$ under the prevailing reaction conditions. Preferred oxidation catalysts include, as the catalytically active component, a metal selected from Group VIII of the Periodic Table of the Elements, and or base metal oxides such as oxides of chromium, manganese, iron, cobalt, nickel, copper and zinc. More preferred catalysts for use in the process comprise a metal selected from palladium, platinum and rhodium, and/or base metal oxides such as oxides of iron, cobalt, and copper. Other known oxidation catalysts may also be used, such as vanadium oxides and cerium oxides.

The catalytically active metal is most suitably supported on a carrier. Suitable carrier materials are well known in the art and include the refractory oxides, such as silica, alumina, titania, zirconia, tungsten oxides, and mixtures thereof. Mixed refractory oxides, that is refractory oxides comprising at least two cations, may also be employed as carrier materials for the catalyst.

The catalytically active metal may be deposited on the carrier by techniques well known in the art. A most suitable technique for depositing the metal on the carrier is impregnation, which technique typically comprises contacting the carrier material with a solution of a compound of the catalytically active metal, followed by drying and calcining the resulting material.

The catalyst (catalytically active material and support) is preferably sulfur tolerant. For the purposes of this description, "sulfur tolerant" means the catalyst continues to operate-in-the presence of sulfur.

The catalyst may comprise the catalytically active metal in any suitable amount to achieve the required level of activity. Typically, the catalyst comprises the active metal in an amount in the range of from 0.01 to 20% by weight, preferably from 0.02 to 10% by weight, more preferably from 0.1 to 7.5% by weight.

Any suitable reaction regime may be applied in the process in order to establish contact between the reactants and the catalyst. One suitable regime is a fluidized bed, in which the catalyst is employed in the form of particles fluidized by a stream of gas. A preferred reaction regime for use in the process is a fixed bed reaction regime, in which the catalyst is retained within a reaction zone in a fixed arrangement. Pellets of catalyst may be employed in the fixed bed regime, retained using fixed bed reaction techniques well known in the art. Alternatively, the fixed arrangement may comprise the catalyst in the form of a monolithic structure. Suitable monolithic structures include refractory oxide monoliths and ceramic foams.

Subsequent to oxidation of sulfur compounds in the hydrocarbon gas stream to $SO_x$ products, these sulfur oxides are removed from the hydrocarbon stream. This is accomplished by placing an adsorbent trap downstream from the oxidation process whereby the $SO_x$ products contact with the adsorbent to trap and remove the sulfur oxides from the hydrocarbon stream. While the adsorbent material is not particularly limited so long as it is capable of adsorbing $SO_x$ at the prevailing conditions, the sulfur oxide traps preferably comprise alkali metal oxides, alkali earth metal oxides and/or base metal (Fe, Ni, Cu, Zn) oxides, which oxides are preferably supported on porous materials such as silica, alumina, etc. Under conditions where $H_2S$ is formed, the trap may further comprise and any effective $H_2S$ adsorbing material, such as zinc oxide. The form of the $SO_x$ and $H_2S$ adsorbent materials is not particularly limited. Preferred forms include pellets and washcoated monolithic structures.

In a preferred embodiment, the desulfurized hydrocarbon stream is reformed into carbon monoxide and/or hydrogen as, for example, by either or both reactions (1) or (2) above. A pure hydrogen stream has particular use in fuel cells for the generation of electricity. A discussion of generating hydrogen for fuel cell operation is given in "The generation of hydrogen for the solid polymer membrane fuel cell", Robert J. Farrauto, Engelhard Corp., Mar. 13, 2000 and presented at the C.R. Acad. Sci. Paris, Serie llc, Chimie/ Chemistry 3 (2000) 573–575.

The principle of operation of a fuel cell is simple. Hydrogen gas is electrocatalytically oxidized to hydrogen ions at the anode composed of Pt deposited on a conductive carbon. The protons pass through a membrane of a fluoropolymer of sulfonic acid called a proton exchange membrane. At the Pt on carbon cathode, $O_2$ from air is electrocatalytically reduced and combines with the protons producing $H_2O$. The electrons flow through the external circuit. The cells are stacked in series to generate higher voltages.

The mixture of carbon monoxide and hydrogen prepared by reformation of the treated hydrocarbon is particularly suitable for use in the synthesis of hydrocarbons, for example by means of the Fischer-Tropsch synthesis, or the synthesis of oxygenates, for example methanol. Processes for the conversion of the mixture of carbon monoxide and hydrogen into such products are well known in the art.

EXAMPLE 1

Gas Chromatography (GC) is used to analyze the inlet and outlet to a partial oxidation catalyst. The inlet gas contains methane and 16 ppmV each of COS, ethylmercaptan, dimethylsulfide, and tetrahydrothiophene. The catalyst is platinum supported on 20% $ZrO_2$ impregnated $SiO_2$ (Pt/20% $ZrO_2$—$SiO_2$) catalyst (80 g/ft$^3$ Pt). Air is added to the gas such that the O2 to carbon ratio in the feed is 0.02. The mixture of feed gas and air is passed over the catalyst at 275° inlet temperature and 20,000/hr space velocity. The pressure is ambient (1 atmosphere). GC analysis (FIGURE) of the outlet to the catalyst shows that the organic sulfur compounds in the feed are all converted to an inorganic sulfur compound. GC-MS analysis further confirms that $SO_2$ the only sulfur compound formed.

EXAMPLE 2

In this example, the same methane feed containing the same concentration of sulfur compounds as in Example 1 is provided with air at the same $O_2/C$ ratio and treated with the same catalyst and conditions as in Example 1. A 30% Cs/alumina trap is placed downstream of the catalyst. The trap is supported on a monolith with a loading of 1 g/in$^3$, and operated at 3000/hr space velocity. The outlet temperature of the trap is measured at 370° C. No sulfur was observed at the outlet of the Cs trap (<10 ppb S) until breakthrough is observed after 26 hours. The Cs/alumina trap has a trapping capacity for $SO_2$ of 2.7 g S per 100 g Cs/alumina trap.

EXAMPLE 3

In this example, desulfurization of methane is achieved with the same oxidation catalyst as used in Example 1. 5.25 ppmV each of COS, ethylmercaptan, dimethylsulfide and tetrahydrothiophene were included in the methane feed stream. Inlet temperature, space velocity and the $O_2/C$ ratio were the same as in Example 1. A downstream trap of 20% K/alumina having a trap capacity of 5.9 g S/100 g trap was used to capture the oxidized sulfur species. The test was run for the first 35 hours at a space velocity for the catalyst of 20,000/hr. For the last hour the time on stream, the catalyst was operated at 10,000/hr. Sulfur is not detected at the exit of the trap until the trap capacity is expended after 36 hours on stream.

EXAMPLE 4

This example illustrates the conversion and interconversion of sulfur compounds at high concentrations of organic sulfur in a methane-propane mixture (Table 1). Natural gas is composed of methane and lower concentrations of heavier hydrocarbons such as ethane, propane, butane, etc. In this example, methane is combined with propane, carbon dioxide, and air to give a composition 81% methane, 3% propane, 4% $CO_2$, 8.6% air. The resulting $O_2/C$ ratio is 0.02. Sulfur compounds are added to the mixture at 16.7 ppmV each carbonylsulfide, ethylmercaptan, dimethylsulfide, and tetrahydrothiophene. The catalyst is similar to the one used in Example 1, except that the Pt loading is 68 g/ft$^3$, operated at 20,000/hr. The trap is comprised of ⅛" pellets of 20% K/alumina, operated at a space velocity of 1510/hr. Note that the total sulfur concentration is 150 ppmw with respect to organic carbon. This is 5 to 6 times higher than the maximum concentration of sulfur in natural gas. COS and ethylmercaptan were not detected at the outlet at any time ([S]<0.005 ppmV). We postulate that the thiophene is a dehydrogenation product of tetrahydrothiophene. No sulfur compounds are detected downstream of the trap at 325° C. at any time on stream to 127 hours.

TABLE 1

| Time on stream (hr:min) | Catalyst inlet T (° C.) | DMS Outlet (ppmV) | DMS % conversion | tHt outlet (ppmV) | tHt % conversion | Thiophene outlet (ppmV) | Total S Outlet (ppmV) | Total S % conversion |
|---|---|---|---|---|---|---|---|---|
| 24:45 | 275 | 0.056 | 99.7 | 0.013 | 99.9 | 0.002 | 0.071 | 99.9 |
| 49:00 | 275 | 0.055 | 99.7 | 0.018 | 99.9 | 0.002 | 0.075 | 99.9 |
| 73:18 | 275 | 0.248 | 98.5 | 0.183 | 98.9 | 0.023 | 0.455 | 99.3 |
| 97:30 | 275 | 0.496 | 97.0 | 0.479 | 97.1 | 0.055 | 1.03 | 98.4 |
| 121:20 | 275 | 0.248 | 98.5 | 0.229 | 98.6 | 0.025 | 0.50 | 99.2 |

TABLE 1-continued

| Time on stream (hr:min) | Catalyst inlet T (° C.) | DMS Outlet (ppmV) | DMS % conversion | tHt outlet (ppmV) | tHt % conversion | Thiophene outlet (ppmV) | Total S Outlet (ppmV) | Total S % conversion |
|---|---|---|---|---|---|---|---|---|
| 23:14 | 300 | ND | 100 | ND | 100 | ND | ND | 100 |
| 47:00 | 300 | ND | 100 | ND | 100 | ND | ND | 100 |
| 71:46 | 300 | 0.007 | 100 | ND | 100 | ND | 0.007 | 100 |
| 96:02 | 300 | 0.015 | 99.9 | <0.010 | 100 | ND | 0.017 | 99.9 |
| 125:53 | 300 | 0.008 | 100 | ND | 100 | 0.025 | 0.033 | 100 |

EXAMPLE 5

This example illustrates the conversion of sulfur compounds in methane using a non-precious metal catalyst ($V_2O_5$). The catalyst is from BASF (O 4-115), a Cs promoted $V_2O_5$ catalyst, crushed pellets operated at a space velocity=1500/hr. The trap downstream of the catalyst is monolith supported 20% K/alumina 1 g/in$^3$, operated at 1880/hr. The gas composition is: 89% methane, 8.6% air, N2 (not including $N_2$ from air); $O_2$/organic C=0.020. Sulfur species and concentrations are 12.5 ppmV each COS, ethylmercaptan (EM), dimethylsulfide (DMS), tetrahydrothiophene (tHt). The total sulfur concentration is 112 ppmw with respect to the organic carbon. This is 3 to 4 times higher than the maximum expected sulfur concentration in natural gas. COS and ethylmercaptan were not detected at the outlet at any time ([S]<0.005 ppmV). The GC analysis is performed after 15 minutes at each temperature. We postulate that the thiophene is a dehydrogenation product of tetrahydrothiophene. The apparent conversion at 250° C. and then increase in breakthrough S concentration up to 325° C. is due to adsorption on the catalyst at 250° C. followed by desorption as the temperature is increased.

certain applications, fuel cells need to load-follow and, thus, the natural gas flow rate will need to vary as the system adjusts power to meet load demands. Typical load following will require a turn down ratio of 8.

The data are average values of analyses obtained every 15 minutes for 24 hours. The catalyst is the same as that in Example 1 (Pt/20% $ZrO_2$—$SiO_2$, 80 g/ft$^3$ Pt). Trap: 20% K/alumina supported on a monolith at 1 g/in$^3$, 1880/hr; sulfur species and concentrations: 12.5 ppmV each COS, ethylmercaptan (EM), dimethylsulfide (DMS), tetrahydrothiophene (tHt); Gas composition: 87% methane, 0.1% to 0.2% hexane, 8.6% air, 1.5% $CO_2$, $N_2$ (not including $N_2$ from air); $O_2$/organic C=0.020. Comments: total sulfur is 112 ppmw with respect to the organic carbon. COS and ethylmercaptan were not detected time on stream ([S]<0.005 ppmV). Catalyst inlet temperature=275° C.

TABLE 2

| Catalyst inlet T (° C.) | DMS Outlet concentration (ppmV) | DMS % conversion | tHt outlet concentration (ppmV) | tHt % conversion | Thiophene outlet concentration (ppmV) | Total S outlet concentration (ppmV) | Total S % conversion |
|---|---|---|---|---|---|---|---|
| 250 | 0.49 | 96.1 | 0.003 | 99.9 | 1.65 | 2.16 | 95.7 |
| 275 | 2.27 | 81.8 | 0.072 | 99.4 | 2.27 | 4.62 | 90.8 |
| 300 | 3.00 | 76.0 | 0.258 | 97.9 | 2.25 | 5.52 | 89.9 |
| 325 | 2.59 | 79.3 | 0.094 | 99.2 | 2.04 | 4.72 | 90.6 |
| 350 | 1.62 | 87.0 | <0.010 | 100 | 1.72 | 3.35 | 93.3 |
| 400 | 0.701 | 94.4 | ND | 100 | 0.72 | 1.42 | 97.2 |
| 425 | 0.316 | 97.5 | ND | 100 | 0.38 | 0.70 | 98.6 |
| 450 | 0.021 | 99.8 | ND | 100 | 0.14 | 0.16 | 99.7 |

EXAMPLE 6

This example illustrates the effect of space velocity on conversion of sulfur compounds at 275° C. in methane. For Sulfur breakthrough was below delectability (<5 ppbV). A slight S breakthrough (<30 ppbV) was observed when the total sulfur inlet concentration was raised to 50 ppmV and the space velocity was at 40,000/hr. At 20,000/hr and 50 ppmV S, no breakthrough was observed.

TABLE 3

| Space velocity (1/hr) | DMS Outlet concentration (ppmV) | DMS % conversion | THt outlet concentration (ppmV) | tHt % conversion | Total S outlet concentration (ppmV) | Total S % conversion |
|---|---|---|---|---|---|---|
| 5,000 | ND | 100 | ND | 100 | 100 | 100 |
| 10,000 | ND | 100 | ND | 100 | 100 | 100 |
| 20,000 | ND | 100 | ND | 100 | 100 | 100 |
| 40,000 | 0.010 | 99.9 | 0.010 | 99.9 | 0.020 | 99.96 |

EXAMPLE 7

This example is directed to desulfurization of LPG. Due to the higher sulfur content of LPG relative to the sulfur content of natural gas and the relative ease with which LPG is oxidized, the conditions for the catalytic desulfurization for LPG are different than for natural gas. A mixture of propane with 5% propylene was doped with 15 ppmV each of COS, ethylmercaptan, dimethylsulfide and tetrahydrothiophene (between 65 and 80 weight part per million (ppmW) with respect to propane+propylene). The gas mixture was combined with air at a variety of oxygen to fuel ratios ranging from 0.03 to 0.05 and the process operated at varying inlet temperatures ranging from 275° C. to 325° C. A downstream trap of Cs/alumina was utilized. Space velocities of 20,000/hr (catalyst) and 3,000/hr (trap) were used. Table 4 sets forth the conditions and results of desulfurization. The system achieves sulfur breakthrough of less than 0.6 ppmV.

Although desulfurization is greater than 90% at the lower space velocity, the sulfur breakthrough is 1 to 2 ppmV, whereas the required outlet S concentration is below 0.1 ppmV (>99.9% conversion)

EXAMPLE 9

As shown in Example 8, LPG desulfurization presents a different challenge than methane because of the higher concentration of sulfur in LPG and the increased reactivity of LPG to air. Accordingly, the process of Example 8 was run with a different catalyst. Thus, a catalyst formulation of $Pt/ZrO_2$—$SiO_2$+$Pt/CeO_2$ was used under the conditions of Example 8.

TABLE 4

| Catalyst inlet T (° C.) | $O_2$/C ratio | DMS Outlet concentration (ppmV) | DMS % Conversion | tHt outlet concentration (ppmV) | tHt % conversion | Thiosphene outlet concentration (ppmV) | Total S outlet concentration (ppmV) | Total S % converstion |
|---|---|---|---|---|---|---|---|---|
| 300 | 0.03 | 1.4 | 91 | 0.23 | 98 | 1.6 | 3.2 | 95 |
| 300 | 0.04 | 0.23 | 98 | 0.07 | 99 | 0.02 | 0.32 | 99 |
| 300 | 0.05 | 0.29 | 98 | 0.022 | 100 | 0.13 | 0.44 | 99 |
| 325 | 0.04 | 0.25 | 98 | 0.02 | 100 | 0.11 | 0.38 | 99 |
| 350 | 0.04 | 0.36 | 98 | 0.01 | 100 | 0.21 | 0.58 | 99 |

EXAMPLE 8

Example 7 illustrating the desulfurization of LPG was repeated except the inlet sulfur concentration was increased from 70 ppmW to 120 ppmW (weight part per million with respect to propane+propylene; this is equal to 100 ppmV for the air-hydrocarbon mixture). An $O_2$/C ratio of 0.04, an inlet temperature of 300° C. and a space velocity varying between 10,000 to 20,000/hr. were used. Results of sulfur breakthrough are shown in Table 5.

TABLE 5

| Space velocity (1/hr) | Time on stream (hr min) | DMS Outlet concentration (ppmV) | DMS % Conversion | tHt outlet concentration (ppmV) | tHt % conversion | Thiophene outlet concentration (ppmV) | Total S outlet concentration (ppmV) | Total S % Conversion |
|---|---|---|---|---|---|---|---|---|
| 20,000 | 0.15 | 3.1 | 88 | 0.7 | 97 | 1.6 | 5.5 | 78 |
| 20,000 | 1.20 | 2.8 | 89 | 0.5 | 98 | 1.0 | 4.3 | 83 |
| 20,000 | 2.20 | 2.5 | 90 | 0.5 | 98 | 0.8 | 3.8 | 85 |
| 10,000 | 0.45 | 1.3 | 95 | 0.1 | 100 | 0.7 | 2.2 | 91 |
| 10,000 | 1.50 | 0.8 | 97 | 0.1 | 100 | 0.5 | 1.4 | 94 |
| 10,000 | 2.50 | 0.6 | 98 | 0.0 | 100 | 0.4 | 1.1 | 96 |

TABLE 6

| Space velocity (1/hr) | Time on stream (hr min) | DMS Outlet concentration (ppmV) | DMS % conversion | tHt outlet concentration (ppmV) | tHt % conversion | Thiophene outlet concentration (ppmV) | Total S outlet concentration (ppmV) | Total S % conversion |
|---|---|---|---|---|---|---|---|---|
| 20,000 | 0.15 | 2.0 | 92 | 0.6 | 98 | 1.7 | 4.4 | 96 |
| 10,000 | 0.45 | 0.6 | 98 | 0.2 | 99 | 1.5 | 2.3 | 98 |

Although changes in selectivity are observed, there is no change in total S breakthrough.

EXAMPLE 10

Example 8 was run except the oxidation catalyst was 1:1 Pt:Pd/WO$_3$—TiO$_2$ (85 g/ft$^3$ total precious metal). The fresh catalyst produces copious quantities of H$_2$S at 300° C. and above. Note that with a trap formulation the includes an H$_2$S trap such as ZnO, the H$_2$S can be removed from the process gas exit stream. When the temperature is decreased to 275° C., the catalyst performance improves dramatically. However, with time on stream, the catalyst loses activity at 275° C. It's performance is recovered by operating at the higher temperature. The values in the table represent average catalyst out concentrations. Methylmercaptan is formed over the catalyst and is identified from its retention time.

TABLE 7

| Time on stream (hr:min) | Catalyst inlet T (° C.) | H$_2$S Outlet (ppmV) | Methyl Mercaptan (ppmV) | DMS Outlet (ppmV) | tHt outlet (ppmV) | Thiophene Outlet (ppmV) | Total S Outlet (ppmV) | Total S % conversion |
|---|---|---|---|---|---|---|---|---|
| 1:00 | 300 | 1.9 | 0.6 | 0.3 | 0.0 | 0.3 | 3.1 | 97% |
| 1:30 | 350 | 2.0 | 0.8 | 0.4 | 0.03 | 1.6 | 4.8 | 95% |
| 32:00 | 275 | 0.0 | 0.0 | 0.03 | 0.0 | 0.01 | 0.04 | 100% |
| 57:00 | 275 | 0.0 | 0.0 | 3.4 | 2.3 | 1.6 | 7.3 | 93% |
| 67:00 | 350 | ND | ND | ND | ND | ND | ND | 100% |

EXAMPLE 11

Example 8 was run except the oxidation catalyst was Pt/TiO$_2$ (71 g/ft$^3$) When this catalyst is operated at 335° C. without first reducing it in H$_2$, the total sulfur out is initially approximately 3 ppmV, mostly as thiophene. Over 36 hours of time on stream, the thiophene out decreases gradually to 0.6 ppmV. When the catalyst is first reduced in H$_2$ before use (10% H$_2$ at 300° C. for two hours), the thiophene out decreases rapidly (within 3 hours time on stream) from 2 ppmV to below detectibility. It gradually increases to 0.3 ppmV; the catalyst activity can be increased by raising the inlet temperature to 350° C., where no sulfur is detected at the trap outlet.

We claim:

1. A method for desulfurizing a hydrocarbon gas, the hydrocarbon gas comprising a hydrocarbon and a sulfur compound, the method comprising:
   (a) increasing the O$_2$ content of the hydrocarbon gas to establish an O$_2$/C mole ratio in the hydrocarbon gas within the range of about 0.01 to less than 0.3; then
   (b) contacting the hydrocarbon gas with an oxidation catalyst, wherein at least a portion of the sulfur compound is oxidized to SO$_x$ and wherein the hydrocarbon gas is within the temperature range of about 200–600° C. when contacting the oxidation catalyst; then
   (c) contacting the SO$_x$ with an adsorbent capable of adsorbing SO$_x$, wherein at least a portion of the SO$_x$ is adsorbed on the adsorbent.

2. The method of claim 1 wherein the oxidation catalyst is sulfur tolerant and is supported by a sulfur tolerant support material.

3. The method of claim 1 wherein the oxidation catalyst comprises a precious metal, a vanadium oxide, a cerium oxide, or a base metal oxide.

4. The method of claim 1 wherein the oxidation catalyst comprises a platinum-containing material.

5. The method of claim 1 wherein the step of increasing the O$_2$ content of the hydrocarbon gas is performed to establish an O$_2$/C mole ratio within the range of about 0.01 to 0.08.

6. The method of claim 1 wherein the step of increasing the O$_2$ content of the hydrocarbon gas is performed to establish an O$_2$/C mole ratio within the range of about 0.01 to 0.04.

7. The method of claim 1 wherein the hydrocarbon gas comprises methane.

8. The method of claim 1 wherein the hydrocarbon gas comprises liquefied petroleum gas.

9. The method of claim 1, wherein the hydrocarbon gas is within the temperature range of about 200–400° C. when contacting the oxidation catalyst.

10. The method of claim 1 wherein the hydrocarbon gas is produced by vaporizing a liquid hydrocarbon.

11. The method of claim 1, wherein the adsorbent capable of adsorbing SO$_x$ is a metal oxide selected from the group consisting of an alkali metal oxide, an alkali earth metal oxide and a base metal oxide.

12. The method of claim 1, further comprising the steps of converting at least a portion of the sulfur compound to H$_2$S, then contacting the H$_2$S with an adsorbent capable of adsorbing H$_2$S.

13. The method of claim 12 wherein the adsorbent capable of adsorbing H$_2$S is zinc oxide.

14. The method of claim 1, further comprising the step of reforming the hydrocarbon gas to produce H$_2$ after step (c).

15. The method of claim 14, further comprising the step of utilizing the H$_2$ in a fuel cell to produce electricity.

16. A method for desulfurizing a hydrocarbon gas, the hydrocarbon gas comprising a hydrocarbon, a sulfur compound and $O_2$, wherein the hydrocarbon gas has an $O_2/C$ mole ratio within a range of about 0.01 to 0.08, the method comprising:
 a) contacting the hydrocarbon gas with an oxidation catalyst, wherein at least a portion of the sulfur compound is selectively oxidized to $SO_x$; then
 b) contacting the $SO_x$ with an adsorbent capable of adsorbing $SO_x$, wherein at least a portion of the $SO_x$ is adsorbed on the adsorbent.

17. The method of claim 16 wherein the oxidation catalyst is sulfur tolerant and is supported by a sulfur tolerant material.

18. The method of claim 16 wherein the oxidation catalyst comprises a precious metal, a vanadium oxide, a cerium oxide or a base metal oxide.

19. The method of claim 16 wherein the oxidation catalyst comprises a platinum-containing material.

20. The method of claim 16 wherein the hydrocarbon gas comprises methane.

21. The method of claim 16 wherein the hydrocarbon gas comprises liquefied petroleum gas.

22. The method of claim 16 wherein the $O_2/C$ mole ratio of the hydrocarbon gas is within the range of about 0.01 to less than 0.3.

23. The method of claim 16 wherein the hydrocarbon gas is within the temperature range of about 200–600° C. when contacting the oxidation catalyst.

24. The method of claim 16 wherein the hydrocarbon gas is produced by vaporizing a liquid hydrocarbon.

25. The method of claim 16 wherein the adsorbent capable of adsorbing $SO_x$ is a metal oxide selected from the group consisting of an alkali metal oxide, an alkali earth metal oxide and a base metal oxide.

26. The method of claim 16, further comprising the steps of converting at least a portion of the sulfur compound to $H_2S$, then contacting the $H_2S$ with an adsorbent capable of adsorbing $H_2S$.

27. The method of claim 26 wherein the adsorbent capable of adsorbing $H_2S$ is zinc oxide.

28. The method of claim 16, further comprising the step of reforming the hydrocarbon gas to produce $H_2$ after step (b).

29. The method of claim 28, further comprising the step of utilizing the $H_2$ in a fuel cell to produce electricity.

* * * * *